(12) United States Patent
Saya et al.

(10) Patent No.: US 9,814,707 B2
(45) Date of Patent: Nov. 14, 2017

(54) CANCER STEM CELL PROLIFERATION INHIBITOR AND INTRACELLULAR ACTIVE OXYGEN ACCUMULATION INDUCER

(71) Applicant: Keio University, Tokyo (JP)

(72) Inventors: Hideyuki Saya, Tokyo (JP); Osamu Nagano, Tokyo (JP); Shogo Okazaki, Tokyo (JP)

(73) Assignee: Keio University, Tokyo (JP)

( * ) Notice: Subject to any disclaimer, the term of this patent is extended or adjusted under 35 U.S.C. 154(b) by 0 days.

(21) Appl. No.: 15/113,932

(22) PCT Filed: Jan. 23, 2015

(86) PCT No.: PCT/JP2015/051761
§ 371 (c)(1),
(2) Date: Nov. 21, 2016

(87) PCT Pub. No.: WO2015/115310
PCT Pub. Date: Aug. 6, 2015

(65) Prior Publication Data
US 2017/0105984 A1   Apr. 20, 2017

(30) Foreign Application Priority Data
Jan. 29, 2014 (JP) ................................ 2014-014857

(51) Int. Cl.
*A61K 31/454* (2006.01)
*A61K 31/655* (2006.01)
*A61K 45/06* (2006.01)

(52) U.S. Cl.
CPC .......... *A61K 31/454* (2013.01); *A61K 31/655* (2013.01); *A61K 45/06* (2013.01)

(58) Field of Classification Search
CPC ..... A61K 31/454; A61K 31/655; A61K 45/06
USPC ..................................................... 514/222.2
See application file for complete search history.

(56) References Cited

U.S. PATENT DOCUMENTS

| | | |
|---|---|---|
| 2009/0076019 A1 | 3/2009 | Tyers et al. |
| 2013/0064814 A1 | 3/2013 | Gray |
| 2013/0065887 A1 | 3/2013 | Bhatia et al. |
| 2013/0331381 A1 | 12/2013 | Bhatia et al. |

FOREIGN PATENT DOCUMENTS

| | | |
|---|---|---|
| CN | 103169703 A | 6/2013 |
| JP | 2012-144498 A | 8/2012 |
| WO | WO-2008/156644 A2 | 12/2008 |
| WO | WO-2012/116432 A1 | 9/2012 |

OTHER PUBLICATIONS

Ishimoto et al., "CD44 variant regulates redox status in cancer cells by stabilizing the xCT subunit of system xc(-) and thereby promotes tumor growth," Cancer Cell. 19(3):387-400 (2011).
Wiklund et al., "Cytotoxic effects of antipsychotic drugs implicate cholesterol homeostasis as a novel chemotherapeutic target," Int J Cancer 126:28-40 (2010).
International Search Report for International Patent Application No. PCT/JP2015/051761, mailed Mar. 24, 2015 (English language translation provided) (5 pages).
Written Opinion of the International Searching Authority for International Patent Application No. PCT/JP2015/051761, mailed Mar. 24, 2015 (No English language translation provided) (3 pages).
Extended European Search Report for European Patent Application No. 15743788.0, dated Apr. 6, 2017 (19 pages).
Chung et al., "Sulfasalazine inhibits the growth of primary brain tumors independent of nuclear factor-kappaB," J Neurochem. 110(1)182-193 (2009) (20 pages).
Nelson et al., "A chemical biology approach to developing STAT inhibitors: molecular strategies for accelerating clinical translation," Oncotarget 2(6):518-524 (2011).
Nelson et al., "The STAT5 inhibitor pimozide displays efficacy in models of acute myelogenous leukemia driven by FLT3 mutations," Genes & Cancer 3(7-8):503-511 (2012).
Nelson et al., "The STAT5 inhibitor pimozide decreases survival of chronic myelogenous leukemia cells resistant to kinase inhibitors," Blood 117(12):3421-3429 (2011).
Shin et al., "Sertindole, a potent antagonist at dopamine $D_2$ receptors, induces autophagy by increasing reactive oxygen species in SH-SY5Y neuroblastoma cells," Biol Pharm Bull. 35(7)1 069-1075 (2012).
Strobl et al., "Inhibition of human breast cancer cell proliferation in tissue culture by the neuroleptic agents pimozide and thioridazine," Cancer Res. 50(17):5399-5405 (1990).

*Primary Examiner* — Kristin Vajda
(74) *Attorney, Agent, or Firm* — Clark & Elbing LLP

(57) ABSTRACT

The present invention is directed to provide cancer stem cell proliferation inhibitors and inducers of intracellular accumulation of reactive oxygen species. To this end, provided are cancer stem cell proliferation inhibitors and inducers of intracellular accumulation of reactive oxygen species in a cancer stem cell each containing pimozide or sertindole as an active ingredient.

6 Claims, 14 Drawing Sheets

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: siRNA

<400> SEQUENCE: 1
guaugacaca uauugcuuct t                                              21

<210> SEQ ID NO 2
<211> LENGTH: 21
<212> TYPE: DNA
<213> ORGANISM: Artificial Sequence
<220> FEATURE:
<223> OTHER INFORMATION: siRNA

<400> SEQUENCE: 2
gaagcaauau gugucauact t                                              21
```

CANCER STEM CELL PROLIFERATION INHIBITOR AND INTRACELLULAR ACTIVE OXYGEN ACCUMULATION INDUCER

CROSS REFERENCE TO RELATED APPLICATIONS

The present application claims priority of Japanese patent application No. 2014-14857 filed Jan. 29, 2014 and the disclosure thereof is hereby incorporated by reference.

TECHNICAL FIELD

The present invention relates to cancer stem cell proliferation inhibitors and inducers of intracellular accumulation of reactive oxygen species.

BACKGROUND ART

In cancer treatments, the presence of cells resistant to chemo- or radiotherapy is responsible for relapse and metastasis and interferes the treatments. Cancer stem cells have been spotlighted as the treatment-resistant cells in recent years. Since cancer stem cells are highly resistant to various stresses, the development of a pharmaceutical agent targeting cancer stem cells is an urgent need for the radical cure of cancers. Investigations of molecular mechanisms underlying the stress resistance of cancer stem cells for the development of therapy targeting the cancer stem cells are, however, just getting started.

CD44, a marker for epithelial cancer stem cells, is known to be involved in their resistance to stresses (Cancer Cell. 2011 Mar. 8; 19(3): 387-400). CD44 has splice variant forms (hereinafter, CD44v) and CD44v stabilizes expression of the cystine transporter xCT on cell membranes. xCT has a function of transporting cystine into cells and the transported cystine is used for production of glutathione (GSH). As a result, the GSH content is increased in cells with high expression of CD44v. It has been believed that since GSH has a strong antioxidative effect and plays a role in reducing stresses of cells, cancer stem cells with a high expression of CD44v are resistant to treatments.

SUMMARY OF THE INVENTION

An object of the present invention is to provide cancer stem cell proliferation inhibitors and inducers of intracellular accumulation of reactive oxygen species.

One aspect of the present invention is a cancer stem cell proliferation inhibitor and an inducer of intracellular accumulation of reactive oxygen species in a cancer stem cell, including a compound having a formula (1) or (2) or a pharmacologically acceptable salt thereof as an active ingredient:

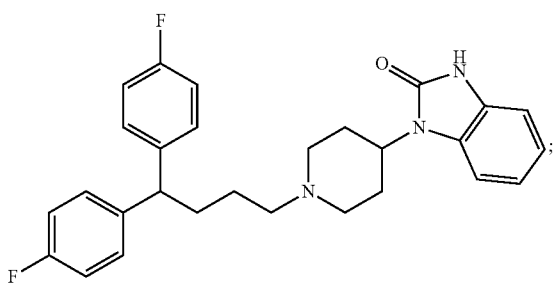

(1)

and

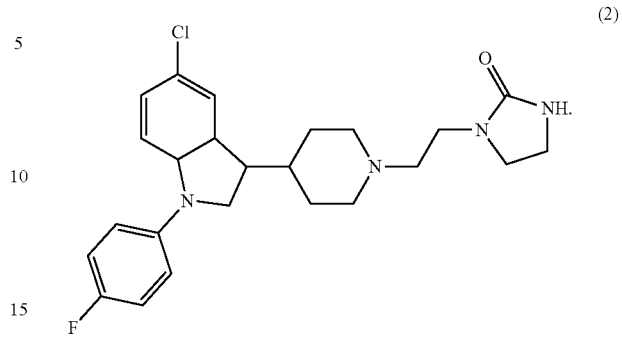

(2)

The cancer stem cell is preferably expressing CD44v. Moreover, the cancer stem cell is preferably contained in a solid cancer. The cancer stem cell proliferation inhibitor and/or the inducer of intracellular accumulation of reactive oxygen species in a cancer stem cell can be administered along with an anticancer agent. The anticancer agent can be sulfasalazine.

Another aspect of the present invention is a method of treating cancer including the step of administering a compound having a formula (1) or (2) or a pharmacologically acceptable salt thereof to a vertebrate having cancer stem cells:

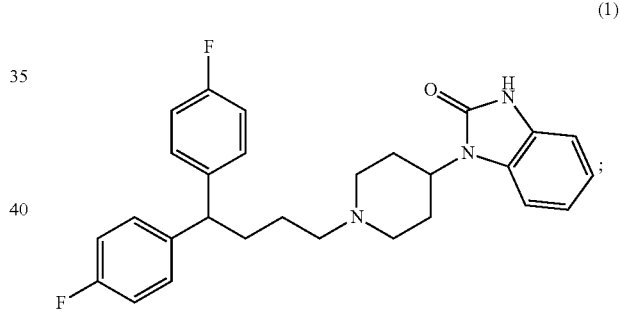

(1)

and

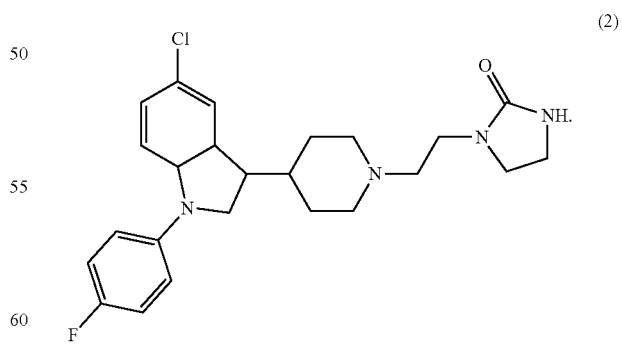

(2)

The cancer stem cell is preferably expressing CD44v. Moreover, the cancer stem cell is preferably contained in a solid cancer. In the administration step, the compound represented by the formula (1) or (2) can be administered along with an anticancer agent. The anticancer agent can be sulfasalazine.

EMBODIMENT OF THE INVENTION

Figure 1:
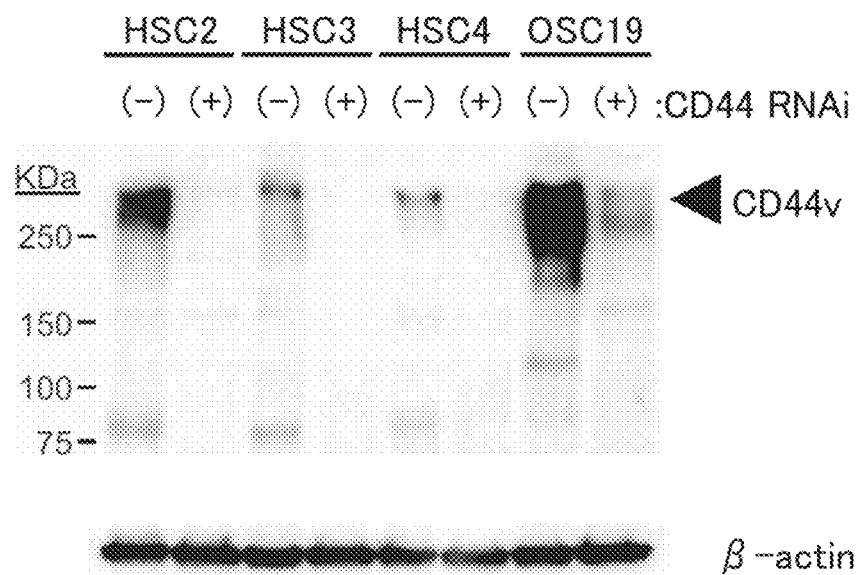
FIG. 1 is a view showing expression level of CD44v in squamous cell carcinoma cell lines HSC4, HSC3, HSC2, and OSC19 in an example of the present invention.

Embodiments of the present invention are described in detail below with reference to Examples. The objects, features, advantages, and ideas of the present invention are apparent to those skilled in the art from the description of this specification. Those skilled in the art can easily reproduce the present invention from the description herein. The embodiments and specific examples described below represent preferable aspects of the present invention, which are given for the purpose of illustration or explanation. The present invention is not limited thereto. It is obvious to those skilled in the art that various changes and modifications may be made according to the description of the present specification within the spirit and scope of the present invention disclosed herein.

Unless otherwise noted in embodiments and examples, all procedures used are according to standard protocols such as J. Sambrook, E. F. Fritsch & T. Maniatis (Ed.), Molecular cloning, a laboratory manual (3rd edition), Cold Spring Harbor Press, Cold Spring Harbor, N.Y. (2001); and F. M. Ausubel, R. Brent, R. E. Kingston, D. D. Moore, J. G. Seidman, J. A. Smith, K. Struhl (Ed.), Current Protocols in Molecular Biology, John Wiley & Sons Ltd., with or without modifications or changes. In addition, commercial reagent kits or measurement instruments are used as described in protocols attached thereto, unless otherwise noted.

Cancer Stem Cell Proliferation Inhibitors and Inducers of Intracellular Accumulation of Reactive Oxygen Species Pharmaceutical agents according to the present invention are cancer stem cell proliferation inhibitors and inducers of intracellular accumulation of reactive oxygen species, which contain at least one of the compounds given in Tables 1 and 2 or a pharmacologically acceptable salt thereof. They may contains a compound or a plurality of compounds.

These compounds can be purchased as bulk drugs, laboratory reagents, or industrial raw materials. Those skilled in the art can obtain a document describing a process of chemical synthesis based on a CAS registration number and produce them according to the description.

These compounds may be derivatized (i.e., addition, substitution, deletion in a part of a molecule).

The pharmacologically acceptable salts in the present invention are not limited as long as they are formed with the compounds of the present invention. Specific examples include addition salts of inorganic acids such as hydrochloride, sulfate, nitrate, hydrobromate, hydroiodide, perchlorate, and phosphate, addition salts of organic acids such as oxalate, maleate, fumarate, and succinate, addition salts of sulfonic acids such as methanesulfonate, ethanesulfonate, benzenesulfonate, p-toluenesulfonate, and camphor sulfonate, and addition salts of amino acids. The salts are preferably hydrochloride, oxalate, maleate, and methanesulfonate.

Furthermore, the compounds of the present invention or the pharmacologically acceptable salts thereof include anhydrides as well as hydrates and polymorphic forms.

TABLE 1

| Compound No. | Compound Name | CAS Registration No. | Structure |
|---|---|---|---|
| SSZ2 | Sulfasalazine | 599-79-1 | 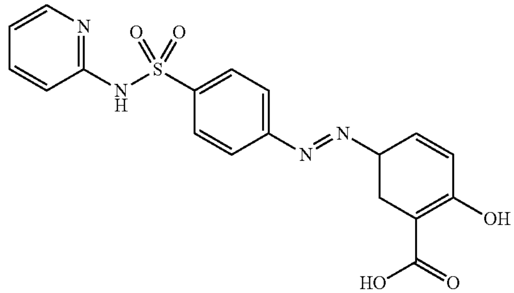 [SMILES: O=C(O)C1=C(O)C=CC(/N=N/c2ccc(S(=O)(=O)Nc3ccccn3)cc2)C1] |
| BSO2 | L-Butionine sulfoximine | 83730-53-4 | 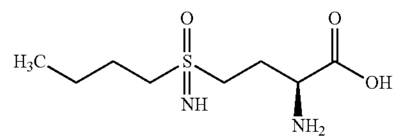 |
| DL042 | Propranolol | 4199-09-1<br>5151-22-9 | 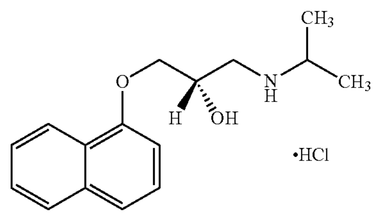 [SMILES: CC(C)NC[C@H](O)COc1cccc2ccccc12 ; Cl] |
| DL053 | Emoren (Oxethazaine) | 13930-31-9<br>126-27-2 | 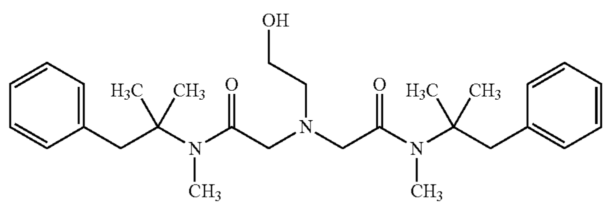 [SMILES: CN(C(=O)CN(CCO)CC(=O)N(C)C(C)(C)Cc1ccccc1)C(C)(C)Cc1ccccc1] |
| DL120 | Amphotericin B | 1397-89-3 | 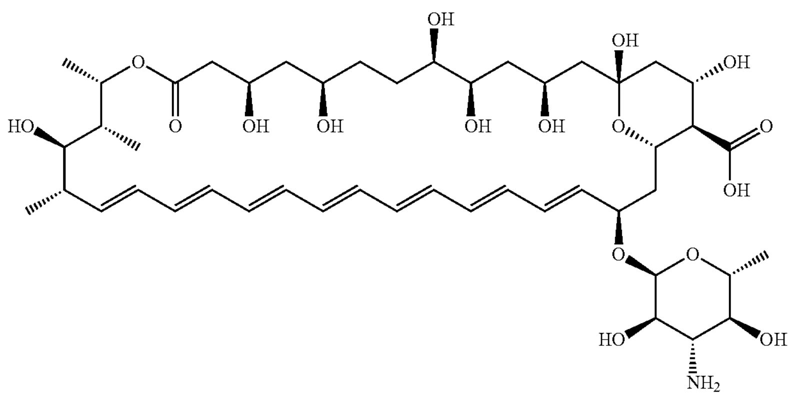 [SMILES: C[C@@H]1[C@H](O)[C@@H](C)/C=C/C=C/C=C/C=C/C=C/C=C/C=C/[C@H](O[C@H]2O[C@H](C)[C@@H](O)[C@H](N)[C@H]2O)C[C@@H]2O[C@](O)(C[C@@H](O)C[C@@H](O)[C@H](O)CC[C@@H](O)C[C@@H](O)CC(=O)O[C@H]1C)C[C@H](O)[C@H]2C(=O)O] |
| DL225 | Telmisartan | 144701-48-4 | 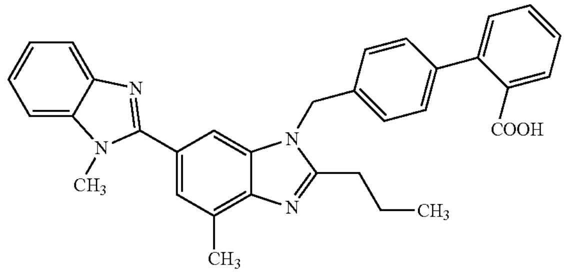 [SMILES: CCCc1nc2c(C)cc(-c3nc4ccccc4n3C)cc2n1Cc1ccc(-c2ccccc2C(=O)O)cc1] |

TABLE 1-continued

| Compound No. | Compound Name | CAS Registration No. | Structure |
|---|---|---|---|
| DL231 | Ampicillin | 69-53-4<br>33993-48-5<br>856649-99-5<br>19379-33-0<br>49841-95-4 | 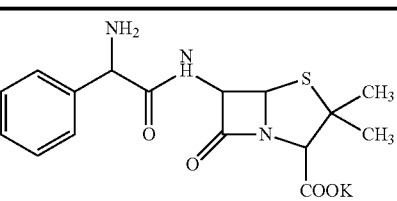 |
| DL242 | 3,4-dihydro-3-methyl-4-oxo-2-phenyl-2H-1-Benzopyran-8-carboxylic acid, 2-(1-piperidinyl)ethyl ester | 1135204-41-9 | 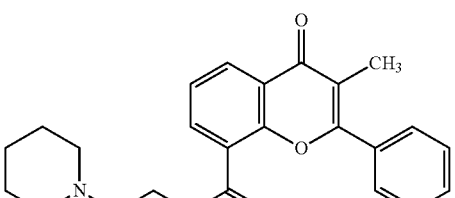 |
| US077 | Pimozide | 2062-78-4 | 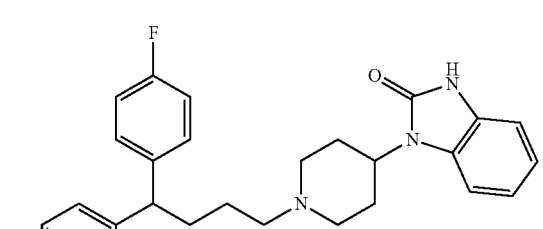 |

TABLE 2

| Compound No. | Compound Name | CAS Registration No. | Structure |
|---|---|---|---|
| SER | Sertindole | 106516-24-9 | 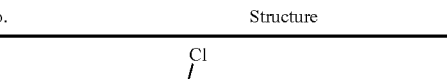 |

In particular, US077 (pimozide) is preferable because it has been used domestically and abroad for the treatment of mental disorders and therefore safety and blood kinetics have been clarified; besides, it is not expensive.

Moreover, SER (sertindole) has also been approved and clinically used as a drug for the treatment of mental disorders in Europe and Australia. Its safety in human has been proven.

Cancer stem cells refer to cancer cells that are particularly resistant to treatments in cancer tissues, and the cancer stem cells targeted by the pharmaceutical agents according to the present invention are preferably those expressing CD44v. Cancers having the cancer stem cells are not specifically limited but are preferably solid cancers. Examples include colorectal adenocarcinoma, gastric adenocarcinoma, breast adenocarcinoma, lung adenocarcinoma, pancreatic adenocarcinoma, and squamous cell carcinoma of the head and neck.

Anticancer Agent

To use the aforementioned compounds as medicament, they can be formulated into dosage forms such as tablets, fine powders, granules, powders, capsules, syrups, emulsions, and suspending agents by an ordinary method for the pharmaceutical agents of the present invention. The pharmaceutical agents of the present invention are produced using a pharmaceutically acceptable additive known to those skilled in the art, such as an excipient and a carrier.

The subject to which the pharmaceutical agent of the present invention is administered is not specifically limited as long as the subject is a vertebrate, but is preferably a human cancer patient. By administering the pharmaceutical agent of the present invention to the cancer patient, it is possible to inhibit proliferation of cancer stem cells in the cancer and induce intracellular accumulation of reactive oxygen species in the cancer stem cells, reducing resistance to stress of the cells.

A necessary dose of the pharmaceutical agent according to the present invention can be administered to the subject in the effective dose range using a suitable route. The effective dose can be appropriately determined by a physician or a veterinarian in consideration of, for example, the dosage form, administration route, age and weight of the subject, and disease conditions of the subject. The dose of the compound(s) is preferably 0.3 mg/kg or more, more preferably 0.5 mg/kg or more, and most preferably 0.8 mg/kg. This amount is preferably 2 mg/kg or less, more preferably 1.5 mg/kg or less, and most preferably 1.3 mg/kg or less. The route of administration is not specifically limited. For example, the compound(s) may be administered orally, parenterally by intraperitoneal or intravenous injection or infusion or directly into the cancer by injection or the like.

The pharmaceutical agent of the present invention can be administered along with other conventional anticancer agent(s), as a pharmaceutical agent for combined use which enhances the effect(s) of the anticancer agent(s). The combined use in this context is preferably simultaneous administration of the agents at the same timing, but they may be administered independently and sequentially as long as a subsequent one is administered within a period during which the action of the previously administered one lasts. Examples of the anticancer agent for the combined use include, but not limited to, cyclophosphamide, dacarbazine, chlorambucil, methotrexate, cytarabine, actinomycin D, bleomycin, doxorubicin, vincristine, vinblastine, cisplatin, oxaliplatin, carboplatin, irinotecan, streptozotocin, paclitaxel, docetaxel, etoposide, gemcitabine, bevacizumab, rituximab, Brefeldin A, trastuzumab, imatinib, pemetrexed, capecitabine, bortezomib, leuprorelin, erlotinib, sunitinib, cetuximab, goserelin, dasatinib, sorafenib, and 5-FU.

By being continuously administered after the treatment using conventional anticancer agents, the pharmaceutical agent according to the present invention can affect cancer stem cells that cannot be killed by the conventional anticancer agents to suppress relapse and metastasis of the cancer.

EXAMPLES

Experimental Example 1

In this Example, expression level of CD44v, GSH content, and sensitivity to the anticancer agent, cisplatin were examined for the oral squamous cell carcinoma cell lines HSC2, HSC3, HSC4, and OSC19.
(Method)
First, cell lines in which CD44 expression was suppressed were constructed using HSC2, HSC3, HSC4, and OSC19. Specifically, siRNA against CD44 made by annealing oligonucleotides having the following sequences purchased from Japan Bio Services Co., LTD. was lipofected into HSC2, HSC3, HSC4, and OSC19 cells using Lipofectamine RNAi MAX (Invitrogen) for 72 hours to obtain clones in which CD44 expression is suppressed.

```
                                          (SEQ ID NO: 1)
(Sense)
5'-GUAUGACACAUAUUGCUUCTT-3'

(SEQ ID NO: 2)
(Antisense)
5'-GAAGCAAUAUGUGUCAUACTT-3'
```

In these clones, suppression of CD44 expression was confirmed. Specifically, their cell lysates in a RIPA buffer were subjected to immunoblotting.

Next, GSH levels in the cells were measured using GSH-Glo™ Glutathione Assay (Promega) to examine the correlation with the CD44v expression. Furthermore, in order to examine the sensitivity of the cell lines in which CD44 expression is suppressed to cisplatin, each cell line was seeded onto a 96-well plate at 2000 cells/well and cisplatin was added the following day at concentrations of 1, 2.5, 5, and 7.5 μM. After 72 hours, the cell viability was measured using Celltiter-Glo (Promega).
(Results)
As shown in FIG. 1, CD44v was expressed in all of HSC2, HSC3, HSC4, and OSC19 cells, but the CD44v expression level was significantly higher in OSC19. It was also confirmed that CD44v expression was decreased by suppressing CD44 expression in all cancer cells tested.

Figure 2:
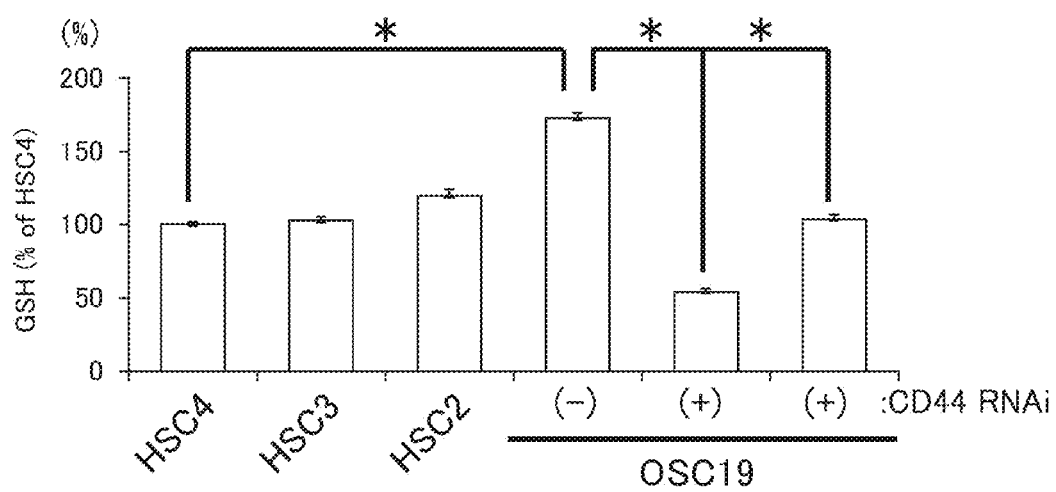
FIG. 2 is a graph showing glutathione contents of squamous cell carcinoma cell lines HSC4, HSC3, HSC2, and OSC19 in an example of the present invention.

Next, GSH contents of the HSC2, HSC3, HSC4, and OSC19 cell lines are shown in FIG. 2. The GSH content is represented relative to the GSH content of HSC-4 defined as 100%. For OSC19, data obtained with and without the CD44 knockdown using RNAi are indicated by (+) and (−), respectively.

As shown in FIG. 2, the GSH content of OSC19 cells was significantly higher than those of HSC2, HSC3, and HSC4 cells and showed correlation with the expression level of CD44v. The suppression of CD44 expression in OSC19 cells resulted in reduction of the GSH content. As apparent from the above, overexpression of CD44 increases GSH content of the cells.

Figure 3:
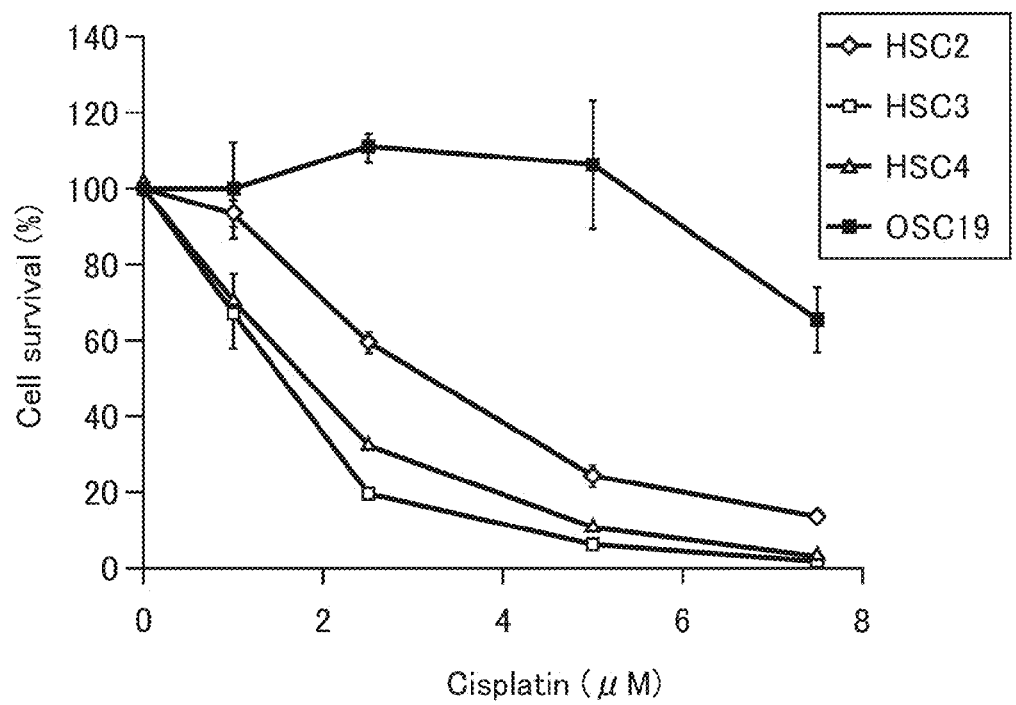
FIG. 3 is a graph showing viability of squamous cell carcinoma cell lines HSC4, HSC3, HSC2, and OSC19 incubated in mediums supplemented with various concentrations of cisplatin for 72 hours in an example of the present invention.

Viability of HSC2, HSC3, HSC4, and OSC19 cells with cisplatin added to the medium is shown in FIG. 3. As shown in FIG. 3, OSC19, which has a significantly higher GSH content than HSC2, HSC3, and HSC4, was significantly lower in sensitivity to cisplatin as compared with HSC2, HSC3, and HSC4.

As apparent from the above, OSC19 has a high GSH content because of the high expression of CD44v and therefore has a feature of the cancer stem cells that are resistant to conventional anticancer agents. Experiments were performed as follows using HSC4 as a representative of ordinary cancer cells and OSC19 as a representative of cancer stem cells.

Experimental Example 2

This Experimental example shows inhibitory effect on cell proliferation and inductive effect on intracellular accumulation of reactive oxygen species, of the compounds given in Table 1.
(Method)
OSC19 and HSC4 cells were seeded onto 96-well plates at 3000 cells/well and 2000 cells/well, respectively and started to be incubated. Two days after the beginning of the incubation, each compound given in Table 1 was added at 10 μM and a control was prepared with no addition of these compounds. Forty-eight hours later, the cells were fixed using 4% PFA-PBS and their nuclei were stained with Hoechst33342. Fluorescence intensity of Hoechst33342 was measured using a plate reader and viability of the cells incubated with each compound was calculated relative to the number of survived control cells defined as 100%. Furthermore, OSC19 selectivity of the compounds was evaluated by calculating a ratio of the viability of HSC4 cells and that of OSC19 cells.

Next, change in level of reactive oxygen species by the compounds having a high selectivity to OSC19 was examined. OSC19 cells were seeded onto 24-well glass-bottomed plate at $1\times10^5$ cells/well, and each compound was added at 10 µM on the following day. Subsequently, the cells were incubated for 24 hours, stained with 2′,7′-dichloro-dihydro-fluorescein-diacetate (H2DCFDA), which is a redox fluorescence indicator, and observed under a fluorescence microscope. In addition, their ability of inducing the reactive oxygen species was evaluated according to the fluorescence intensity.

(Results)

Figure 4:
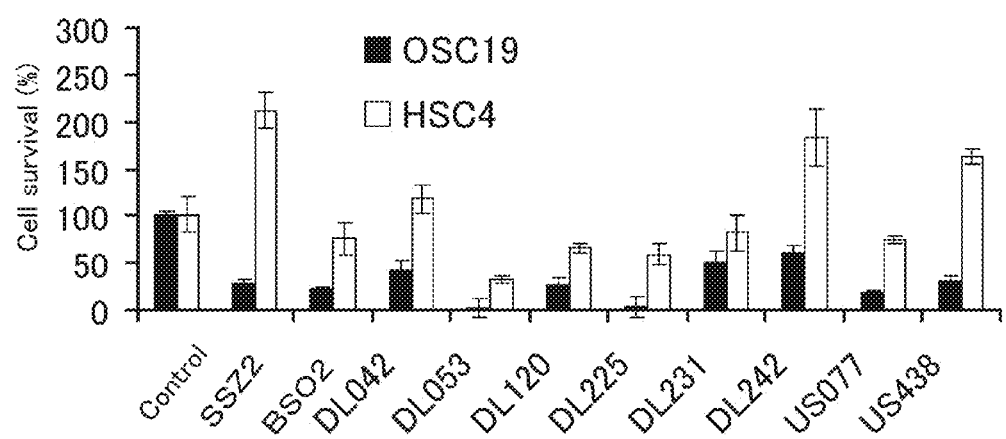
FIG. 4 is a graph showing viability of squamous cell carcinoma cell lines HSC4 and OSC19 incubated in mediums supplemented with various compounds in an example of the present invention.
Figure 5:
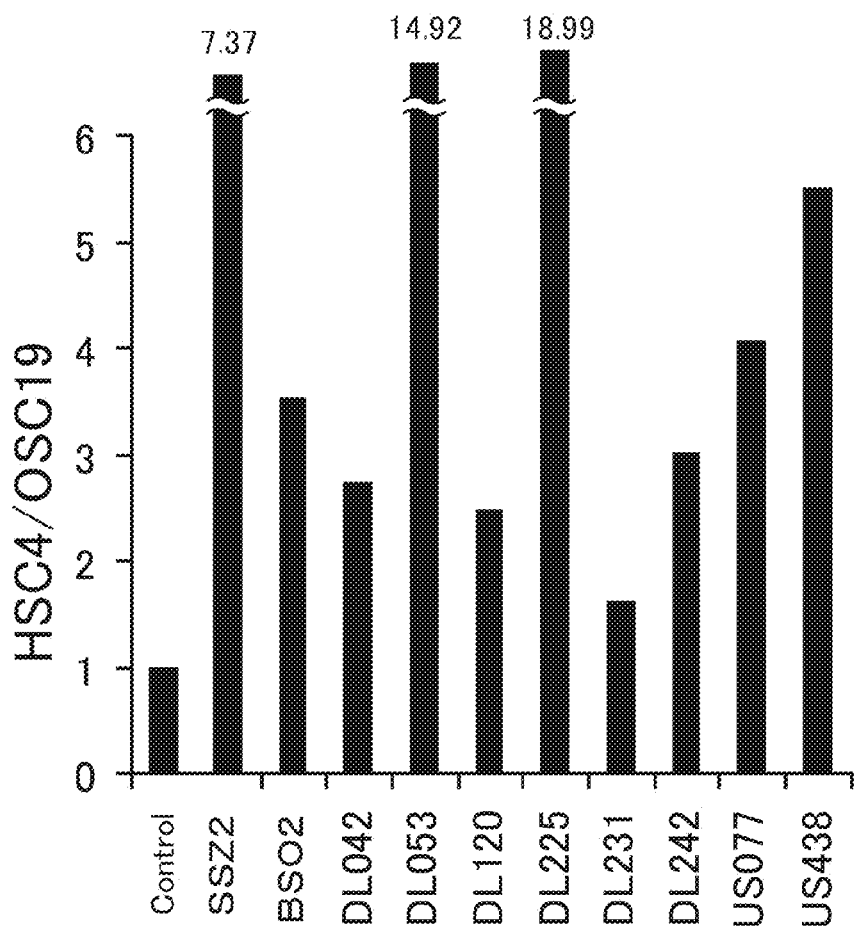
FIG. 5 is a graph showing ratios of viability of squamous cell carcinoma cell lines HSC4 and OSC19 incubated in mediums supplemented with various compounds in an example of the present invention.

Viability of HSC4 and OSC19 cells incubated in a medium supplemented with each of the compounds is shown in FIG. 4. FIG. 5 shows ratios of viability of OSC19 cells relative to that of HSC4 cells. The compounds in Table 1 investigated herein all have a greater inhibitory effect on proliferation of the OSC19 cells than on the HSC4 cells.

Figure 6:
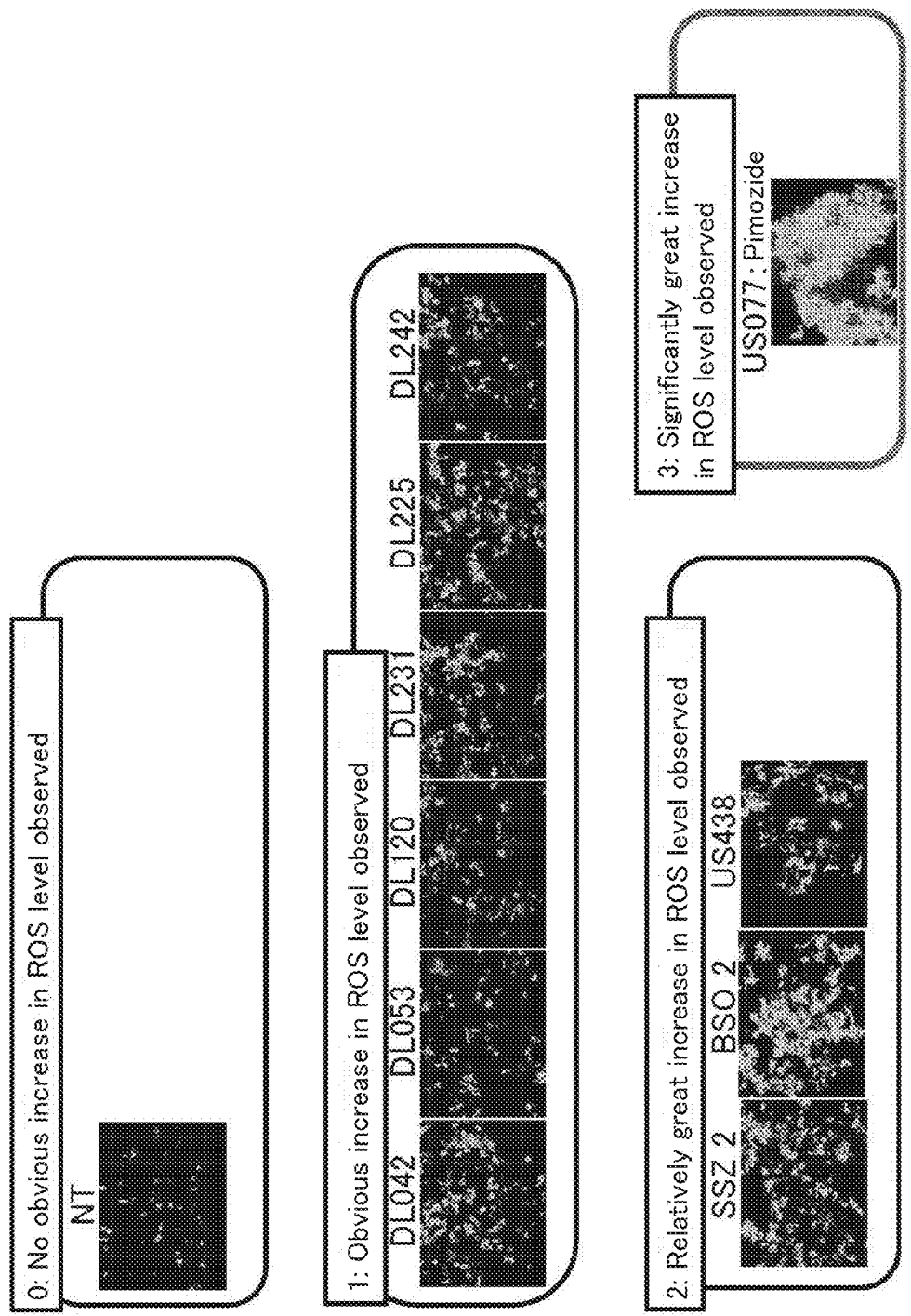
FIG. 6 is micrographs showing changes in level of reactive oxygen species (ROS) when squamous cell carcinoma cell line OSC19 was incubated in mediums supplemented with various compounds in an example of the present invention.

FIG. 6 is fluorescence micrographs of OSC19 cells treated with the compounds given in Table 1, showing the increase in ROS in OSC19 cells scored on 4 rating scales. NT represents a fluorescence micrograph of OSC19 cells that were not treated with any compound given in Table 1. The "4 rating scales" are as follows.

0: No obvious increase in ROS level observed.
1: Obvious increase in ROS level observed
2: Relatively great increase in ROS level observed
3: Significantly great increase in ROS level observed As can be seen from the figure, all compounds given in Table 1 increased the ROS level in OSC19. In particular, a significantly great increase in ROS level was found in OSC19 cells incubated in a medium containing pimozide.

Experimental Example 3

This Experimental example shows an inhibitory effect on cell proliferation by US077 (pimozide).

(Method)

Cell viability was examined for OSC19 and HSC4 cells incubated in a medium supplemented with US077 (pimozide). As a positive control, OSC19 and HSC4 cells were also incubated in a medium supplemented with sulfasalazine, which has been demonstrated to exhibit a selective inhibitory effect on CD44v-positive cancer cells (see, Cancer Cell. 2011 Mar. 8; 19(3): 387-400), to examine the cell viability.

OSC19 and HSC4 cells were seeded in 96-well plates at 3000 cells/well and 2000 cells/well, respectively. On the following day, 0 µM (no addition), 0.3 µM, 1 µM, 3 µM, 10 µM, 30 µM, or 100 µM of pimozide or 0 µM (no addition), 10 µM, 30 µM, 100 µM, 300 µM, or 1000 µM of sulfasalazine were added. Then, the cells were incubated for 72 hours and cell viability was measured using Celltiter-Glo (Promega).

Next, $1\times10^6$ OSC19 cells were subcutaneously transplanted into nude mice. After 5 days of transplantation, 1 mg/kg of pimozide or saline was intraperitoneally administered once daily to day 35. Short and long axes of each tumor were measured once every 3-4 days and a volume of the tumor was calculated using the following equation.

Tumor volume=(long axis×(short axis)$^2$)/2

Specific tumor volume=tumor volume on the day measured/tumor volume at the beginning of administration Statistic analysis of the tumor volume was performed using Two-way ANOVA. Each tumor was removed after the treatment experiments and the mass of the tumor was measured. Statistic analysis of the tumor mass was performed using a t-test. The results are shown in FIGS. 9 and 10, respectively.

(Results)

Figure 7:
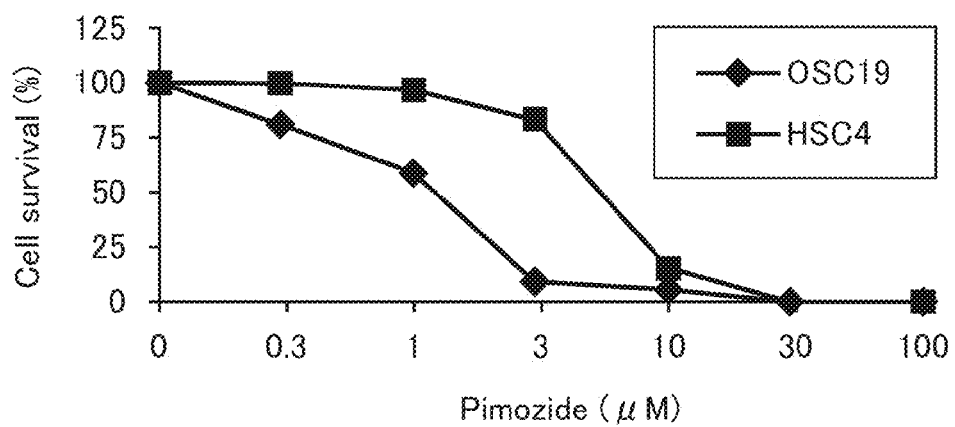
FIG. 7 is a graph showing viability of squamous cell carcinoma cell lines HSC4 and OSC19 incubated in mediums supplemented with various concentrations of pimozide for 72 hours in an example of the present invention.
Figure 8:
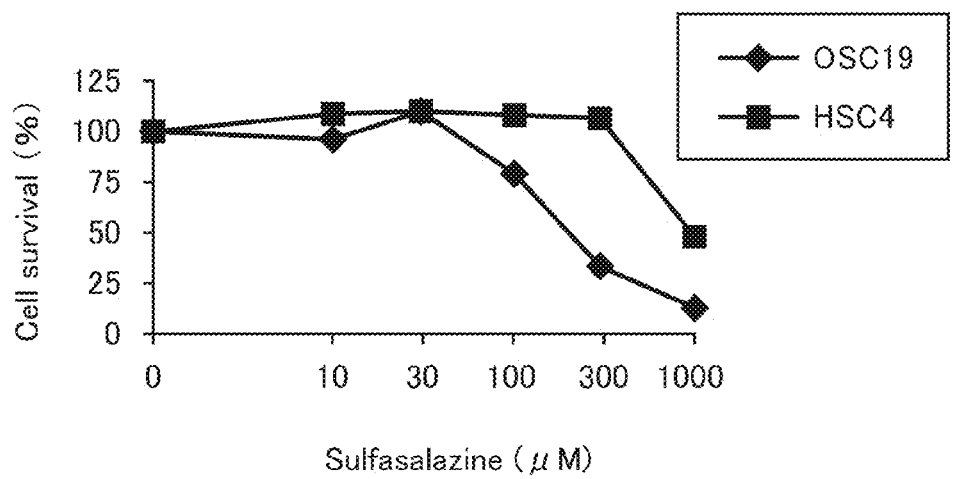
FIG. 8 is a graph showing viability of squamous cell carcinoma cell lines HSC4 and OSC19 incubated in mediums supplemented with various concentrations of sulfasalazine for 72 hours according to an example of the present invention.

FIGS. 7 and 8 show viability of HSC4 and OSC19 cells with various amount of pimozide or sulfasalazine. As shown in FIG. 7, the OSC19 cells have a higher sensitivity to pimozide than the HSC4 cells. As shown in FIG. 8, the OSC19 cell also exhibited a higher sensitivity to sulfasalazine than the HSC4 cells, but pimozide has an inhibitory effect on cell proliferation at a lower concentration than sulfasalazine.

Figure 9:
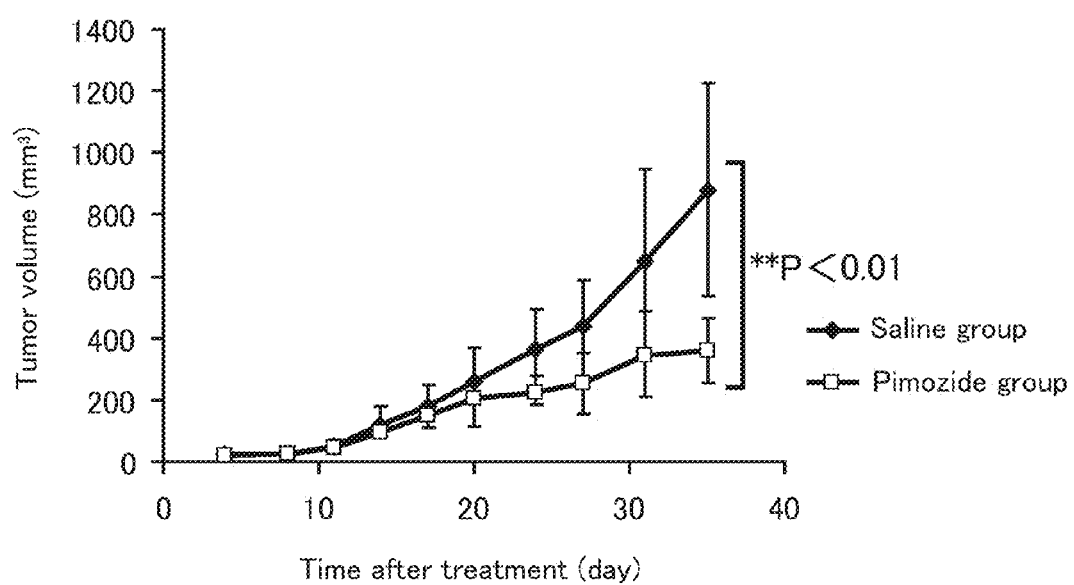
FIG. 9 is a graph showing change in tumor volume in mice when $1\times10^6$ OSC19 cells were subcutaneously transplanted to and then saline or pimozide was intraperitoneally administered once daily after 5 days of transplantation in an example of the present invention.
Figure 10:
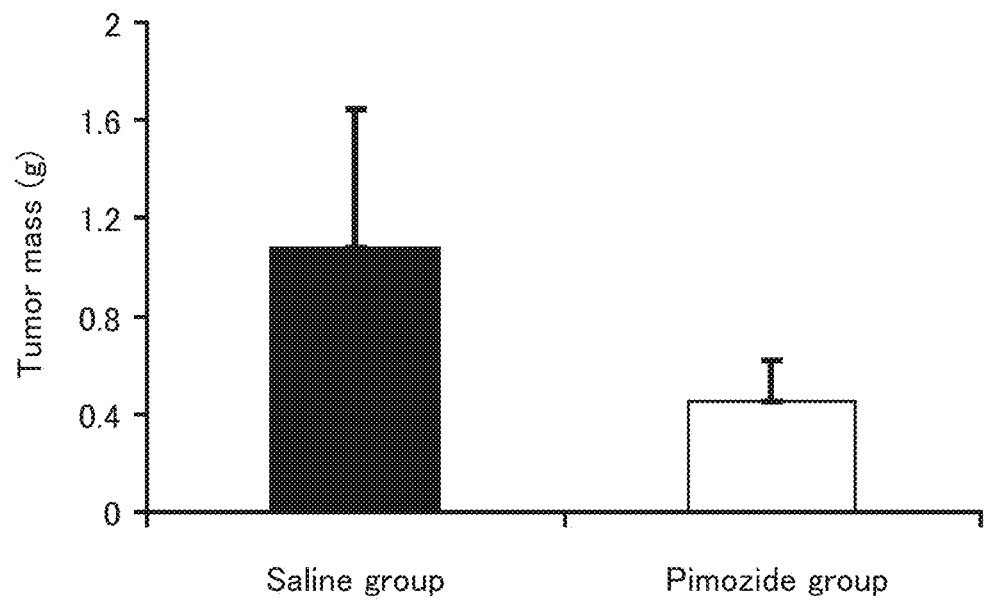
FIG. 10 is a graph showing changes in tumor mass in mice when $1\times10^6$ OSC19 cells were subcutaneously transplanted to and then saline or pimozide was intraperitoneally administered once daily after 5 days of transplantation in an example of the present invention.

FIG. 9 shows change in tumor volume in nude mice that were subjected to subcutaneous transplantation of $1\times10^6$ OSC19 cells and then intraperitoneal administration of 1 mg/kg of pimozide or saline once daily after 5 days of transplantation. FIG. 10 shows the mass of tumor on day 35. As can be seen from these figures, the administration of pimozide resulted in the inhibition of proliferation of the OSC19 cells.

As apparent from the above, pimozide has an inhibitory effect on proliferation selectively of CD44v-positive cancer stem cells, thereby proliferation of cancers can be inhibited efficiently.

Experimental Example 4

This Experimental example shows an inductive effect on intracellular accumulation of reactive oxygen species by US077 (pimozide).

(Method)

OSC19 and HSC4 cells were seeded onto 24-well glass-bottomed plate at $1\times10^5$ cells/well. On the following day, 0 µM (no addition), 1 µM, 3 µM, or 10 µM of pimozide or 300 µM of sulfasalazine was added. Subsequently, the cells were incubated for 24 hours, stained with H2DCFDA to visualize intracellular reactive oxygen species, and observed under a fluorescence microscope.

(Result)

Figure 11:
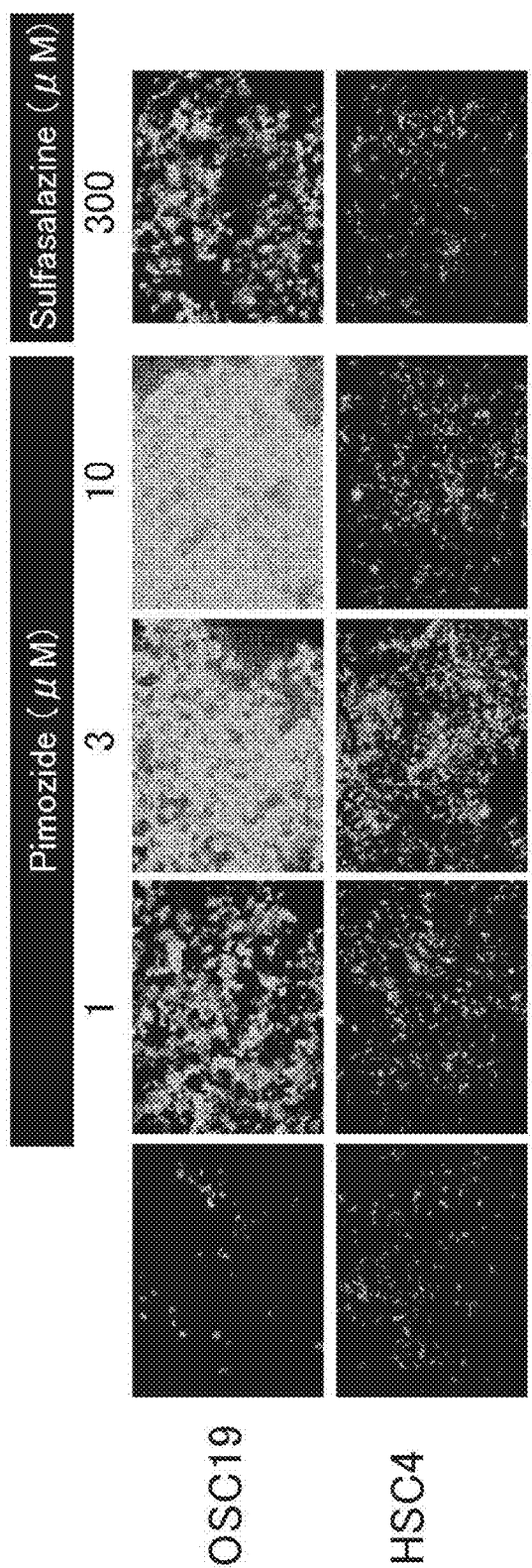
FIG. 11 is figures showing ROS amounts in squamous cell carcinoma cell lines HSC4 and OSC19 with the addition of pimozide or sulfasalazine in an example of the present invention.

FIG. 11 shows fluorescence micrographs of the OSC19 and HSC4 cells incubated in a medium supplemented with 1 µM, 3 µM, or 10 µM of pimozide or 300 µM of sulfasalazine. As shown in the figure, pimozide has an inductive effect on intracellular accumulation of reactive oxygen species selectively in OSC19 cells as in the case of sulfasalazine, but pimozide can exhibit a significantly greater inductive effect on intracellular accumulation of reactive oxygen species at a significantly lower concentration as compared with sulfasalazine.

As described above, pimozide is a compound capable of effectively inhibiting stress resistance which is a characteristic of the cancer stem cells.

Experimental Example 5

Next, an exemplified inhibitory effect on cell proliferation by sertindole is described.

(Method)

OSC19 and HSC4 cells were seeded in 96-well plates at 3000 cells/well and 2000 cells/well, respectively, and started to be incubated. Two days after the beginning of the incubation, 0 µM (no addition), 0.19 µM, 0.56 µM, 1.67 µM, 5.00 µM, 15.00 µM, or 45.00 µM of sertindole was added. After 72-hour incubation, the number of the survived cells was measured using Celltiter-Glo (registered trademark) (Luminescent Cell Viability Assay; Promega). A ratio of the number of the survived cells to the number of the cells on the first day of incubation was calculated as a cell viability value.

(Results)

Figure 12:
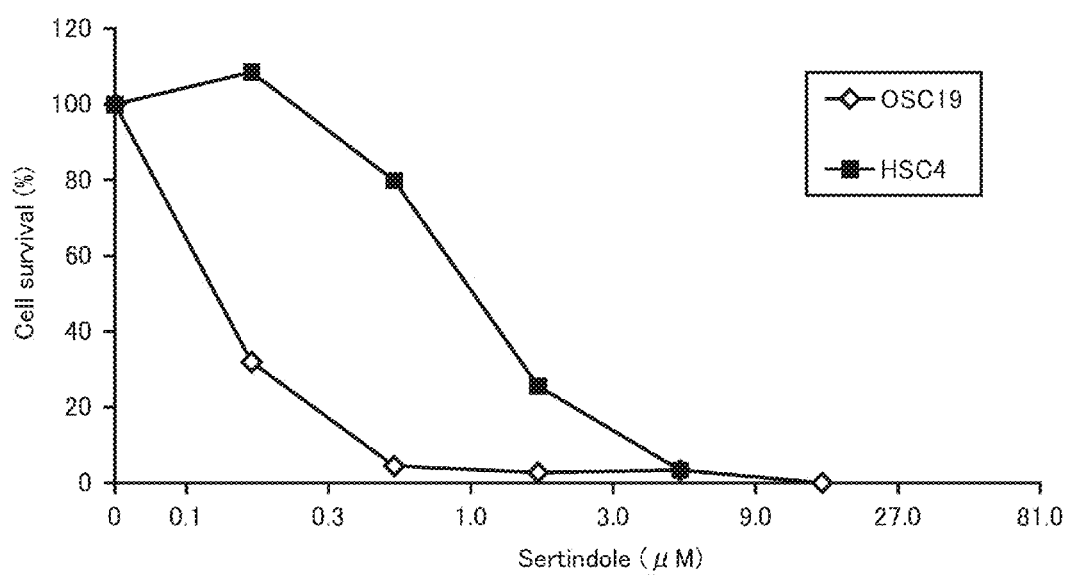
FIG. 12 is a figure showing viability of squamous cell carcinoma cell lines HSC4 and OSC19 incubated in a sertindole-supplemented medium in an example of the present invention.

FIG. 12 show cell viability relative to the concentration of sertindole added to the medium. As can be seen from the figure, cell proliferation was inhibited by the addition of a lower concentration of sertindole for OSC19 than for HSC4.

As described above, sertindole has an more inhibitory effect on proliferation of CD44v-positive cancer stem cells than that of ordinary cancer cells.

Experimental Example 6

Next, an inductive effect on intracellular accumulation of reactive oxygen species by sertindole was examined.
(Method)

OSC19 cells were seeded onto 24-well glass-bottomed plate at 1×10$^5$ cells/well and started to be incubated. Two days after the beginning of the incubation, 0.1 µM, 1 µM, or 10 µM of sertindole or 300 µM of sulfasalazine was added. DMSO was added to the control. The cells were then incubated for 24 hours, and 2',7'-dichloro-dihydro-fluorescein-diacetate (H2DCFDA), which is a redox fluorescence indicator capable of emitting fluorescence when oxidized by reactive oxygen species in cells and Hoechst33342 that stains a cell nucleus were added. A ratio of the number of cells stained with H2DCFDA to the number of cells stained with Hoechst33342 was calculated. The results are given in FIG. 13.

(Results)

Figure 13:
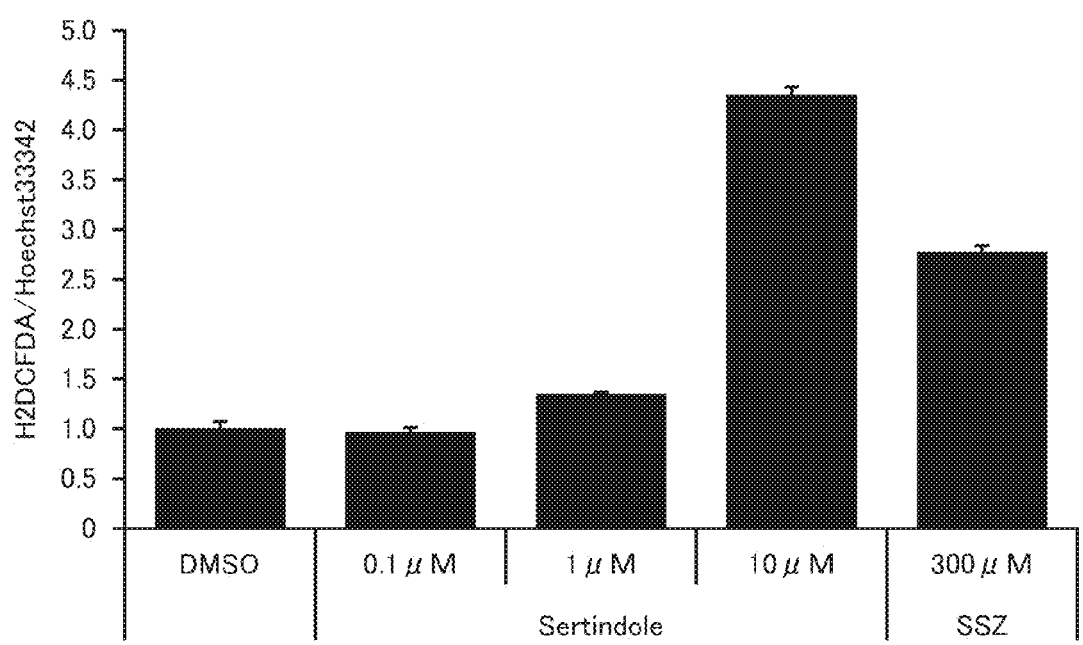
FIG. 13 is a figure showing ratios of the number of cells stained with H2DCFDA relative to the number of cells stained with Hoechst33342 when DMSO, sertindole, or sulfasalazine is added in an example of the present invention.

As shown in FIG. 13, when 10 µM of sertindole was added, the intracellular ROS level was higher as compared with a case where sulfasalazine was added at 30 times higher concentration.

As apparent from the above, sertindole is a compound capable of effectively inhibiting stress resistance which is a characteristic of the cancer stem cells.

Example 7

This Example examined a inhibitory effect on cell proliferation by combined use of pimozide and sulfasalazine.
(Method)

Oral squamous cell carcinoma cell line, OSC19, was seeded onto 96-well plates at 3000 cells/well. On the following day, a combination of 0 µM (no addition; only DMSO), 1 µM, 2 µM, or 3 µM of pimozide, and 0 µM (no addition; only DMSO), 10 µM, 50 µM, 100 µM, 150 µM, or 200 µM of sulfasalazine was added. Subsequently, cells were incubated for 72 hours, and cell viability was measured using a CellTiter-Glo Luminescent Cell Viability Assay kit (Promega). Effects obtained using pimozide and sulfasalazine at different concentrations are shown in a graph in FIG. 14.

(Results)

Figure 14:
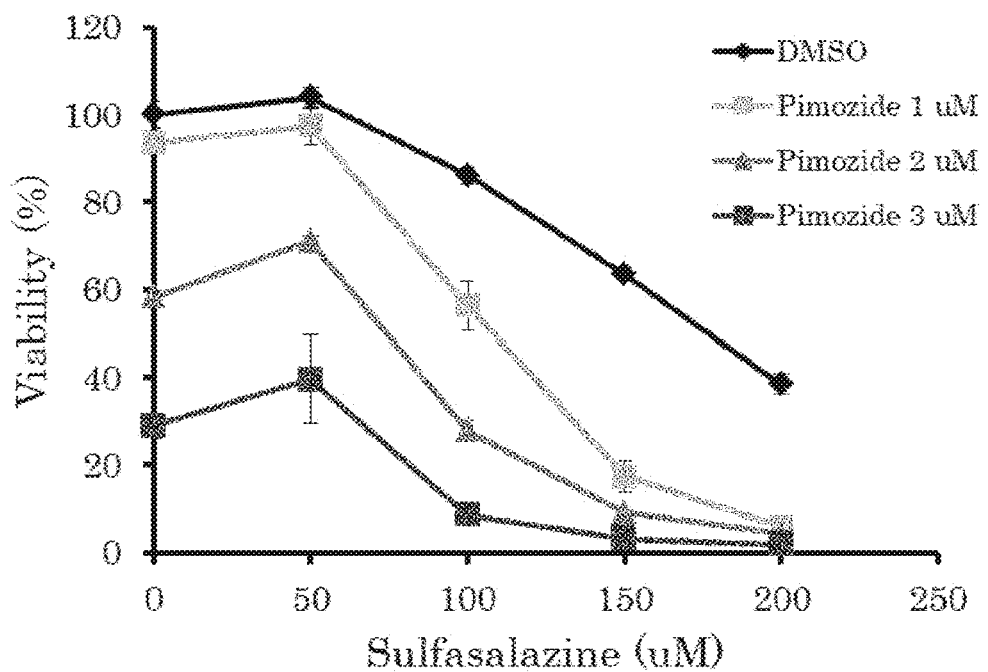
FIG. 14 is a figure showing effects of inhibiting cell proliferation of OSC19 by pimozide and sulfasalazine used in combination in an example of the present invention.

As shown in FIG. 14, synergetic effects of pimozide and sulfasalazine were observed in their combined use. As an example, the mortality of cells with 2 µM of pimozide is about 40% and that with 150 µM of sulfasalazine is about 30%, whereas the mortality of cells when they are combined reaches 90% or higher.

As apparent from the above, pimozide and sulfasalazine have a synergetic inhibitory effect on the cell proliferation.

INDUSTRIAL APPLICABILITY

According to the present invention, it is possible to provide cancer stem cell proliferation inhibitors and inducers of intracellular accumulation of reactive oxygen species.

The invention claimed is:

1. A method of treating a patient with a cancer stem cell expressing CD44v, comprising a step of administering a cancer stem cell proliferation inhibitor, the inhibitor comprising an effective amount of a compound having a formula (1) or (2):

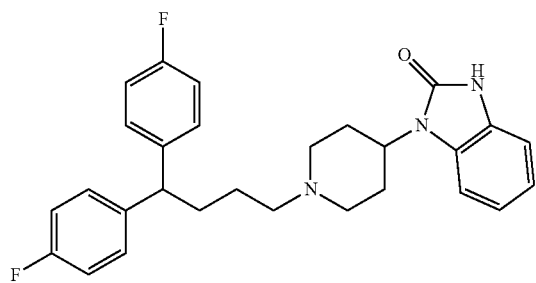

(1)

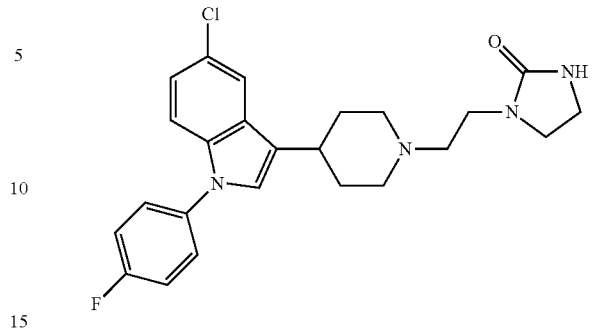

(2)

or a pharmacologically acceptable salt thereof.

2. The method according to claim 1, wherein the cancer stem cell is contained in a solid cancer.

3. The method according to claim 1, wherein the cancer stem cell proliferation inhibitor is administered along with an anticancer agent.

4. The method according to claim 3, wherein the anticancer agent is sulfasalazine.

5. The method according to claim 1, wherein the cancer stem cell proliferation inhibitor induces intracellular accumulation of reactive oxygen species in the cancer stem cell.

6. The method according to claim 1, wherein the cancer stem cell proliferation inhibitor is an anticancer agent.

* * * * *